(12) United States Patent
Sayegh

(10) Patent No.: US 11,903,817 B2
(45) Date of Patent: Feb. 20, 2024

(54) SURGICAL DEVICE AND METHOD FOR IMPLANTING AN ARTIFICIAL CORNEA

(71) Applicant: The Cleveland Clinic Foundation, Cleveland, OH (US)

(72) Inventor: Rony R. Sayegh, Akron, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 153 days.

(21) Appl. No.: 17/541,683

(22) Filed: Dec. 3, 2021

(65) Prior Publication Data
US 2022/0175516 A1 Jun. 9, 2022

Related U.S. Application Data

(60) Provisional application No. 63/120,877, filed on Dec. 3, 2020.

(51) Int. Cl.
*A61F 2/14* (2006.01)
*A61F 9/007* (2006.01)

(52) U.S. Cl.
CPC .............. *A61F 2/142* (2013.01); *A61F 2/148* (2013.01); *A61F 9/007* (2013.01)

(58) Field of Classification Search
CPC ........... A61F 2/142; A61F 2/148; A61F 9/007
See application file for complete search history.

(56) References Cited

U.S. PATENT DOCUMENTS

| | | | | |
|---|---|---|---|---|
| 2,881,500 A | * | 4/1959 | Furness | A61F 2/0095 606/107 |
| 4,470,159 A | * | 9/1984 | Peyman | A61F 2/16 623/5.11 |
| 5,464,417 A | * | 11/1995 | Eick | A61F 9/007 606/166 |
| 6,258,110 B1 | * | 7/2001 | Hellenkamp | A61F 9/013 606/166 |
| 9,095,424 B2 | * | 8/2015 | Kahook | A61F 2/1648 |
| 10,695,166 B2 | * | 6/2020 | Willis | A61F 9/007 |
| 2003/0158560 A1 | * | 8/2003 | Portney | A61F 2/1616 606/107 |
| 2019/0151077 A1 | * | 5/2019 | Chodosh | A61F 2/15 |
| 2019/0307551 A1 | * | 10/2019 | Peyman | A61F 9/0079 |

FOREIGN PATENT DOCUMENTS

| | | | | |
|---|---|---|---|---|
| EP | 1099432 A2 | * | 5/2001 | ............. A61F 9/007 |
| WO | WO-2017201213 A1 | * | 11/2017 | ............. A61B 17/00 |

\* cited by examiner

*Primary Examiner* — Megan Y Wolf
*Assistant Examiner* — Yasniary De La Caridad Morales
(74) *Attorney, Agent, or Firm* — Wentsler LLC

(57) ABSTRACT

A surgical device for implanting an artificial cornea into an eye can comprise an installation tool comprising an implantation end for receiving a back portion of an artificial cornea. The installation tool can further comprise a drive nut positioned above the implantation end. The surgical device can further comprise a thumbscrew that is received within the drive nut. The thumbscrew can be rotatable relative to the drive nut to adjust a position of the thumbscrew. During an implantation procedure, the implantation end with the back portion of the artificial cornea positioned thereon can be inserted into the eye, and the thumbscrew can be rotated relative to the drive nut to interact against a front portion of the artificial cornea to lock the artificial cornea in place.

20 Claims, 9 Drawing Sheets

SURGICAL DEVICE AND METHOD FOR IMPLANTING AN ARTIFICIAL CORNEA

CROSS-REFERENCE TO RELATED APPLICATIONS

This application claims the benefit of U.S. Provisional Application No. 63/120,877, filed Dec. 3, 2020, which is hereby incorporated by reference in its entirety.

FIELD

The present disclosure relates generally to artificial corneal (keratoprosthesis) implants, and more particularly to a surgical device and related method for implanting an artificial keratoprosthesis implant into a human eye.

BACKGROUND

A number of conditions, such as chemical splash to the eye, infections or injuries, can be damaging to the cornea. When damaged, the cornea becomes hazy and less transmissive to light, which reduces vision. In severe cases, the damaged cornea becomes essentially opaque, resulting in substantial impairment and blindness. These cases do not do well with a traditional corneal transplant, and the transplanted cornea frequently becomes hazy again soon after surgery.

Artificial corneal implants, also known as keratoprosthesis implants, have been developed to replace a damaged cornea. FIG. 1 is an exploded perspective view of a conventional combination of an artificial keratoprosthesis implant, also referred to as an artificial cornea 10, and a cornea section 18 previously extracted from a patient's eye. The artificial cornea 10 includes a front portion comprising a front plate 12 which acts as a clear optical cylinder, and a back portion comprising a back plate 14 and locking ring 16. In use, the back portion of the artificial cornea 10 comprising the back plate 14 and locking ring 16 are positioned on an internal side of the extracted cornea section 18. As referenced above, the extracted cornea section 18 may be grayed and opaque, and therefore a vision hole 20 is cut through the damaged extracted cornea section 18 to permit the passage of light. A stem 23 of the front plate 12 is then inserted through the vision hole 20 in the extracted cornea section 18 and through the central openings of the back plate 14 and locking ring 16. After the stem 23 is fully inserted, the locking ring 16 snaps behind a ridge 22 on the stem 23 to lock the implant in place relative to the extracted cornea section 18. Once assembled in this fashion, the artificial cornea 10 is held in place relative to the extracted cornea section 18 and vision is permitted through the extracted cornea section 18 via light passing through the front plate 12 and vision hole 20. Typically, the back plate 14 and locking ring 16 are made of any suitable rigid material commonly used for artificial implants, such as poly(methyl methacrylate) (PMMA), titanium or like material. The front plate 12 is made of a transparent material to permit the passage of light for vision, and PMMA, and other like materials within the material classes of acrylic, Plexiglas, and Lucite, are typical compounds for making the front plate 12.

In conventional surgical techniques for implanting such a device, the cornea section 18 can be cut away and removed from the patient's eye, wherein a gaping hole is left in the eye until the surgical procedure is completed. Then the combination of the extracted cornea section 18 and artificial cornea 10 (shown in FIG. 1) is assembled outside of the patient's eye. Finally, the assembled combination of the extracted cornea section 18 and artificial cornea 10 is implanted back into the patient's eye by suturing the previously extracted cornea section 18 (with attached artificial cornea 10) to the unremoved portion of the eye (typically requiring about 16 sutures).

The conventional surgical techniques described above are highly invasive. Indeed, the eye will be completely open due to the extraction of the cornea section 18, and the suturing of the previously extracted cornea section 18 (with attached artificial cornea 10) back into the eye is an added surgical step. As a result, the complication rate is high, including inflammation, melting of the sutured cornea, and failure of the implant to operate effectively, approaching a total of about 75% chance of complications.

SUMMARY

There are set forth herein surgical devices and methods for implanting an artificial cornea that reduce complications with a less invasive procedure than conventional apparatus and methods. Furthermore, surgical devices and methods for implanting an artificial cornea simplifies the implanting procedure. Some embodiments of the disclosure are discussed below with the understanding that further embodiments may be covered by the claims of the disclosure.

Embodiment 1. A surgical device for implanting an artificial cornea into an eye can comprise an installation tool comprising an implantation end for receiving a back portion of an artificial cornea. The installation tool can further comprise a drive nut positioned above the implantation end. The surgical device can further comprise a thumbscrew that is received within the drive nut. The thumbscrew can be rotatable relative to the drive nut to adjust a position of the thumbscrew. During an implantation procedure, the implantation end with the back portion of the artificial cornea positioned thereon can be inserted into the eye, and the thumbscrew can be rotated relative to the drive nut to interact against a front portion of the artificial cornea to lock the artificial cornea in place.

Embodiment 2. The surgical device of embodiment 1, wherein the implantation end comprises a first seat for receiving a back plate of the back portion of the artificial cornea, and a plurality of guide posts that extend from the first seat to guide locating of the back plate.

Embodiment 3. The surgical device of embodiment 2, wherein each guide post of the plurality of guide posts are positioned between a pair of adjacent guide posts of the plurality of guide posts, wherein each guide post of the plurality of guide posts are twisted 45° relative to each guide post of a corresponding pair of adjacent guide posts.

Embodiment 4. The surgical device of any one of embodiments 2-3, wherein the implantation end further comprises a plurality of guide ridges to further guide locating of the back plate.

Embodiment 5. The surgical device of embodiment 4, wherein the guide ridges comprise tapered ends to aid in inserting the implantation end into the eye.

Embodiment 6. The surgical device of any one of embodiments 2-5, wherein the implantation end further comprises a recessed seat for receiving a locking ring of the back portion of the artificial cornea.

Embodiment 7. The surgical device of any one of embodiments 1-6, wherein the drive nut and the thumbscrew comprise opposing cooperating threads to permit rotating the thumbscrew relative to the drive nut.

Embodiment 8. The surgical device of embodiment 7, wherein the thumbscrew comprises a stem comprising threads opposing threads of the drive nut. The thumbscrew further comprises a cap located on the stem that comprises a gripping portion for rotating the thumbscrew relative to the drive nut. The thumbscrew still further comprises a distal end located opposite from the cap that interacts against a front plate of the front portion of the artificial cornea.

Embodiment 9. The surgical device of embodiment 8, wherein the distal end has a finished surface to prevent scratching the front plate.

Embodiment 10. The surgical device of any one of embodiments 1-9, wherein the drive nut and the implantation end are spaced apart by a distance between 5.2 mm and 12.2 mm.

Embodiment 11. The surgical device of any one of embodiments 1-10, wherein the installation tool comprises titanium or surgical grade stainless steel.

Embodiment 12. The surgical device of any one of embodiments 1-11, wherein the thumbscrew comprises plastic.

Embodiment 13. The surgical device of any one of embodiments 1-12, wherein the installation tool comprises a handle portion that ends in the drive nut, and the handle portion and the implantation end comprise a unitary piece.

Embodiment 14. The surgical device of any one of embodiments 1-12, wherein the installation tool comprises a handle portion that ends in the drive nut, and the handle portion and the implantation end are separate components fixed together at a joint.

Embodiment 15. A method of performing a surgical implantation of an artificial cornea with a surgical device according to any one of embodiments 1-14. The method can comprise the steps of placing a back portion of an artificial cornea onto the implantation end of the installation tool externally from an eye of a patient. The method can further comprise cutting a vision hole into a cornea of the eye and cutting an incision into the eye. The method can further comprise inserting the implantation end with the back portion of the artificial cornea though the incision and into the eye and aligning the back portion of the artificial cornea with the vision hole. The method can further comprise placing a front portion of the artificial cornea over the vision hole in alignment with the back portion. The method can still further comprise rotating the thumbscrew relative to the drive nut to press the front portion toward the back portion to lock the artificial cornea to the cornea of the eye. The method can further comprise moving the implantation end out of the incision to remove the implantation end of the installation tool from the eye while leaving the artificial cornea locked to the cornea of the eye.

Embodiment 16. The surgical implantation method of embodiment 15, wherein the placing the back portion of the artificial cornea comprises placing a back plate of the back portion onto a first seat of the implantation end and using guide posts of the first seat to guide back plate onto the first seat.

Embodiment 17. The surgical implantation method according to embodiment 16, wherein, after placing the back plate, distal ends of the guide posts are flush with an outer surface of the back plate.

Embodiment 18. The surgical implantation method according to any one of embodiments 16-17, further comprising, prior to placing the back plate, placing a locking ring of the back portion of the artificial cornea on a recessed seat of the implantation end.

Embodiment 19. The surgical implantation method of embodiment 18, wherein the rotating the thumbscrew rotates the thumbscrew until the locking ring locks onto the front plate.

BRIEF DESCRIPTION OF THE DRAWINGS

The above and other features and advantages of embodiments of the present disclosure are better understood when the following detailed description is read with reference to the accompanying drawings, in which.

DETAILED DESCRIPTION

Figure 1:
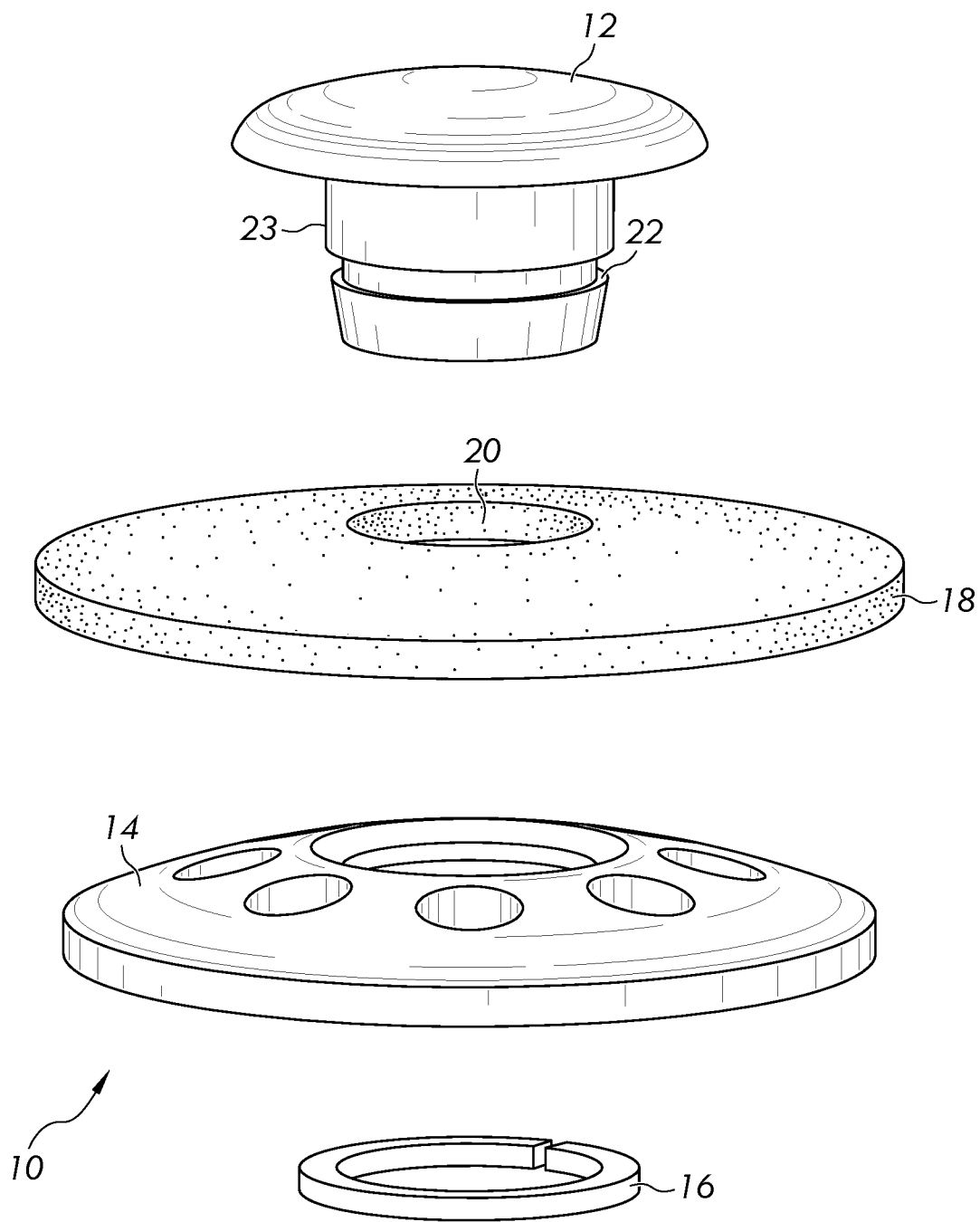
FIG. 1 illustrates an exploded perspective view of a conventional combination of an artificial cornea and a cornea section extracted from a patient's eye.

Embodiments of the present disclosure will now be described with reference to the drawings, wherein like reference numerals are used to refer to like elements throughout. It will be understood that the figures are not necessarily to scale.

Figure 11:
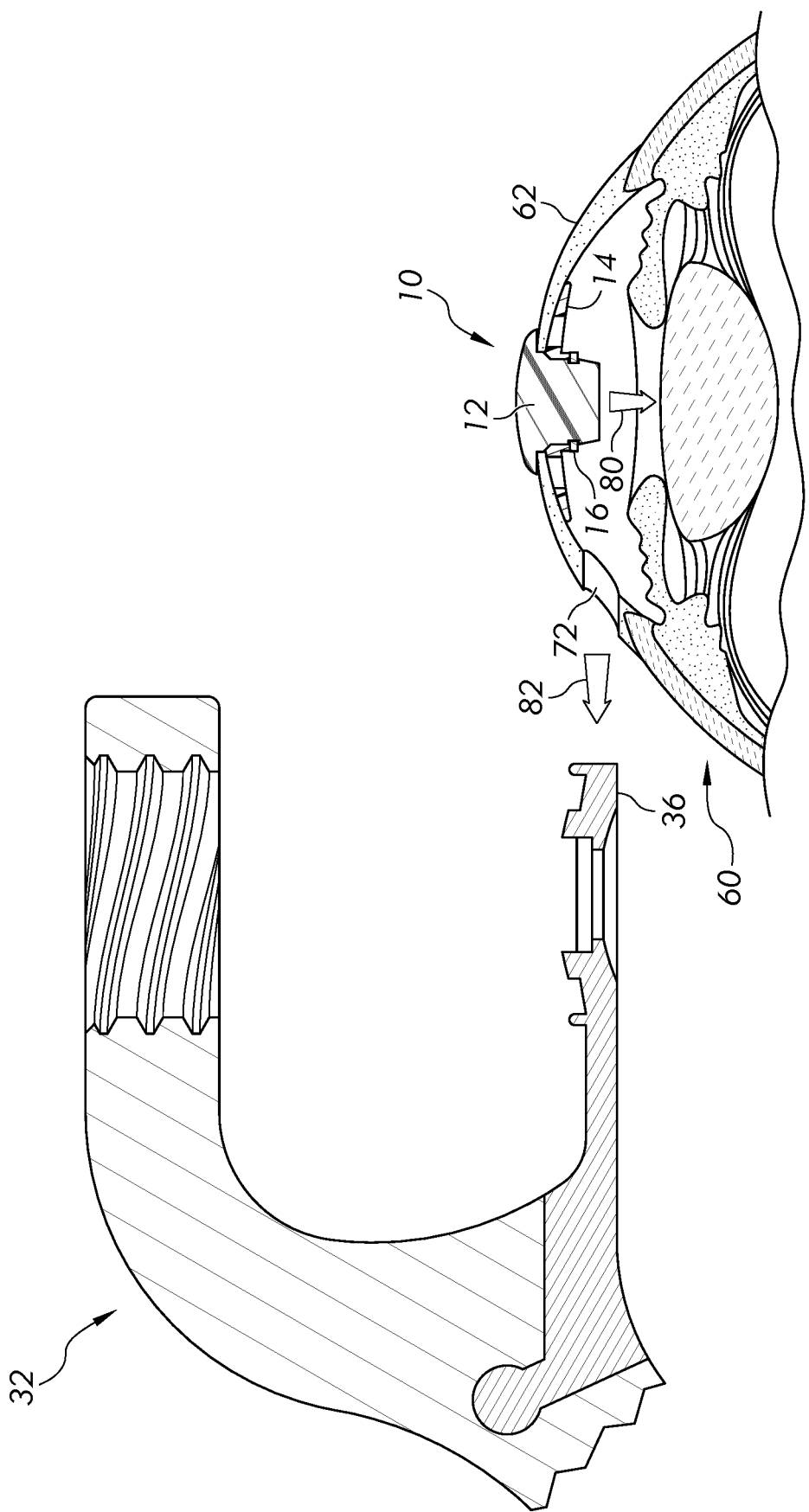
FIG. 11 schematically illustrates moving the implantation end out of the incision to remove the implantation end of the installation tool from the patient's eye while leaving the artificial cornea locked to the cornea of the patient's eye.

The present disclosure provides surgical devices and related methods for implanting an artificial cornea 10 into an eye 60 of a patient as shown in FIG. 11. The present disclosure permits implantation without having to remove or extract a cornea section from the eye for pre-assembly of the artificial cornea as shown exploded in FIG. 1. Rather, methods of implanting the artificial cornea 10 of the disclosure is performed directly on the eye 60 with minimal suturing and without additional surgical steps used in conventional methods. The procedure, therefore, is more efficient, far less invasive, and obviates the need for removal of the cornea section for pre-assembly with the artificial cornea, and therefore should result in a reduced complication rate.

Figure 2:
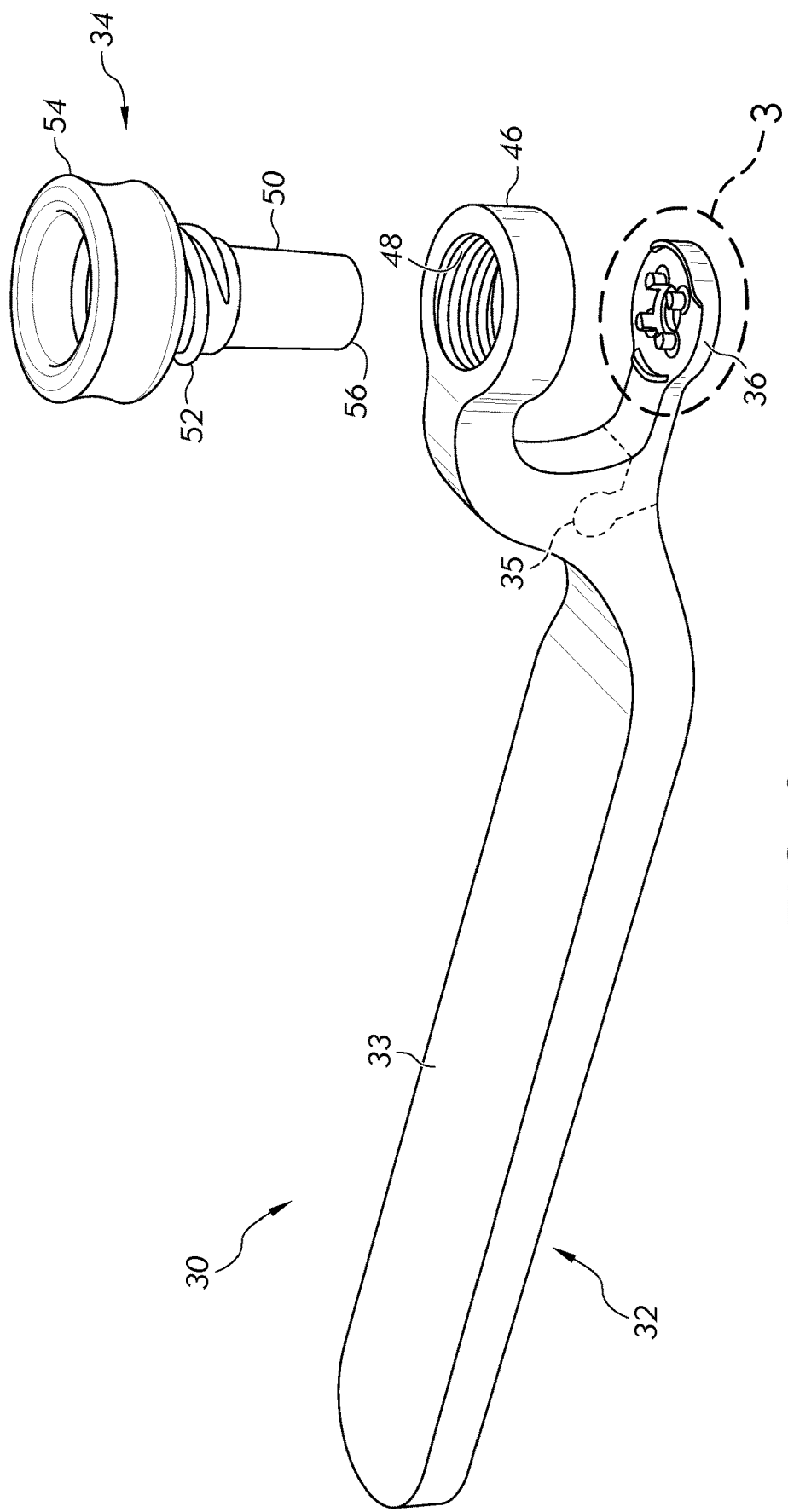
FIG. 2 illustrates an exploded perspective view of a surgical device for implanting an artificial cornea into the eye of the patient in accordance with embodiments of the disclosure.

FIG. 2 illustrates an exploded perspective view of a surgical device 30 for implanting the artificial cornea 10 into the eye 60 of the patient in accordance with embodiments of the disclosure. The surgical device 30 includes an installation tool 32 and a thumbscrew 34. The installation tool 32 has a handle portion 33 and an implantation end 36. The installation tool 32 may be made of any material commonly used for surgical instruments, such as for example a surgical grade stainless steel or titanium. The handle portion 33 and implantation end 36, therefore, may be made of the same material, or alternatively may be made of different materials. In the example of FIG. 2, the handle portion 33 and implantation end 36 are depicted as a unitary piece. In further examples, as indicated by the dashed lines, the handle portion 33 and the implantation end 36 may be separate components fixed together at a joint 35. Providing the handle portion 33 and the implantation end 36 as separate components can allow the implantation end 36 and the handle portion 33 to be made from different materials.

As further illustrated in FIG. 2, the handle portion 33 of the installation tool 32 may further include a drive nut 46. The drive nut 46 is positioned above the implantation end 36, and in exemplary embodiments, a clearance between the implantation end 36 and the drive nut 46 is approximately between 5.2 and 12.2 mm, with the preferred clearance being at or closer to the 12.2 mm end of the range. The drive nut 46 can further include internal threads 48 for mating with external threads 52 of the thumbscrew 34.

Figure 3:
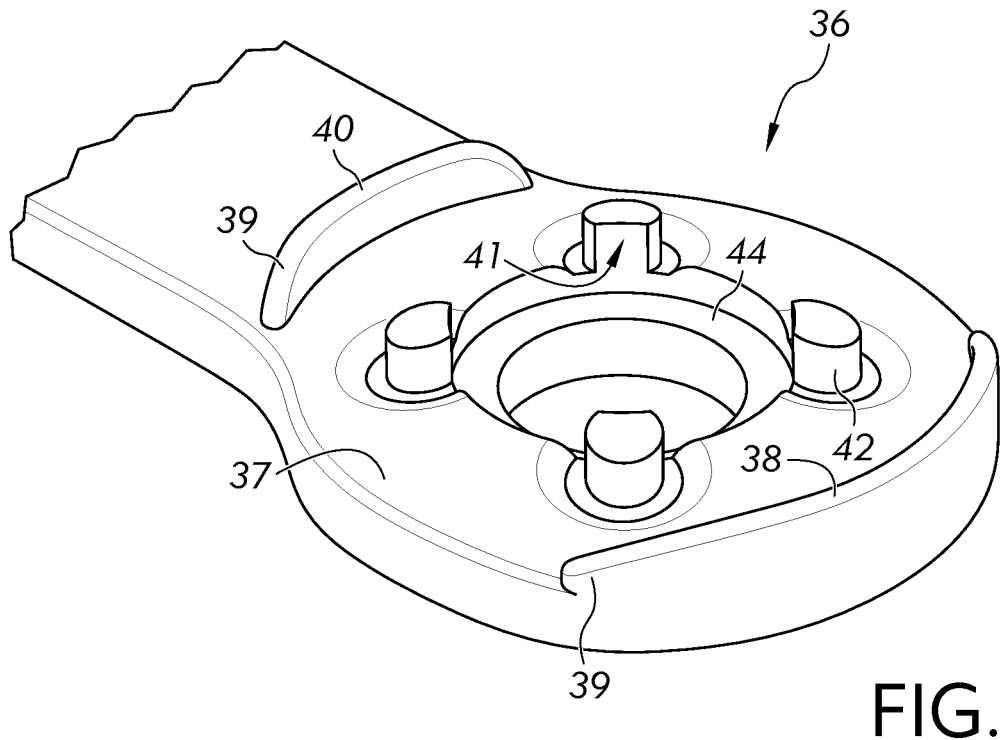
FIG. 3 is an enlarged view of the implantation end of the surgical device taken at view 3 in FIG. 2.
Figure 5:
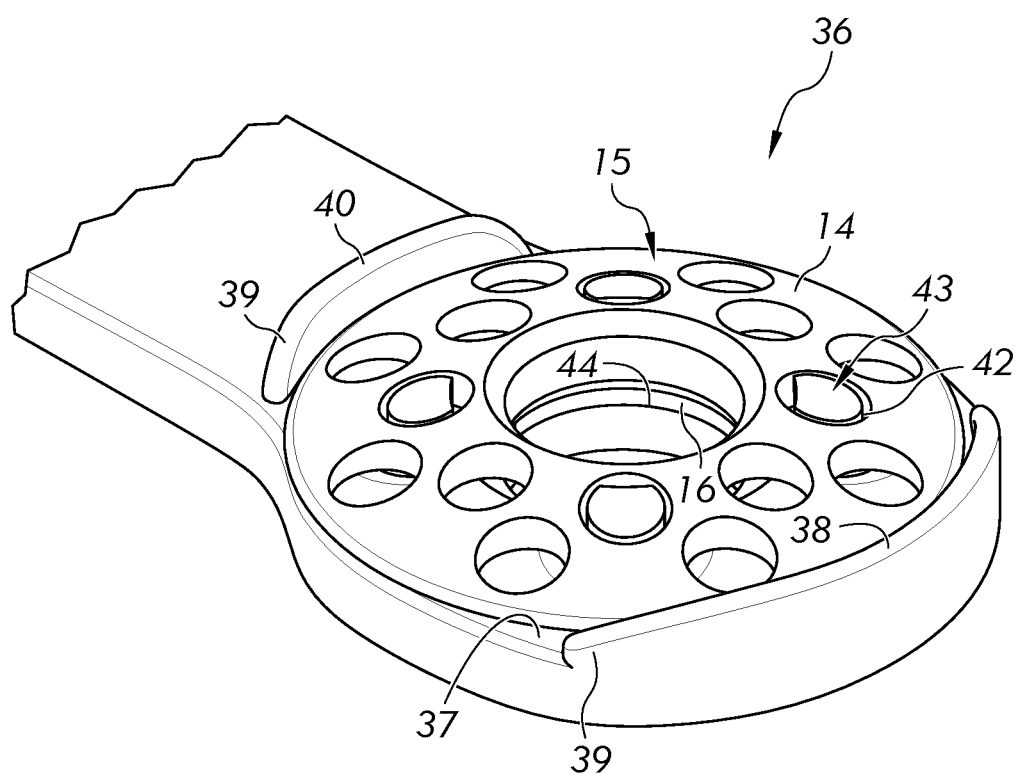
FIG. 5 illustrates another step in a method of performing a surgical implantation of the artificial cornea comprising placing a back plate of the back portion of the artificial cornea onto a first seat of the implantation end using guide posts of the first seat to guide the back plate onto the first seat.

FIG. 3 is an enlarged view of one illustrative embodiment of the implantation end 36 of the installation tool 32 in accordance with aspects of the disclosure. The implantation end 36 may include a first seat 37 that is configured to receive a back plate 14 of a back portion of the artificial cornea 10. The implantation end 36 can also include guide ridges 38, 40 and guide posts 42 configured to guide the location of the back plate 14 of the artificial cornea 10 onto the first seat 37 of the implantation end 36 as shown in FIG. 5. The first seat 37 also may be sized and shaped to have a diameter that is essentially flush with the back plate 14 during use. As further shown in FIG. 5, the guide posts 42 may be sized and shaped such that, after placing the back plate 14 onto the first seat 37 of the implantation end 36, distal ends 43 of the guide posts 42 can be flush with an outer surface 15 of the back plate 14, which may permit easier removal from the eye at the end of the implantation procedure and can provide a clearance relative to the front plate 12 when locking the artificial cornea 10 to the cornea 62 of the patient's eye 60.

As shown in FIG. 3, each guide post 42 of the plurality of guide posts are positioned between a pair of adjacent guide posts 42 of the plurality of guide posts 42. In some embodiments, as shown, each guide post 42 of the plurality of guide posts 42 can be twisted 45° relative to each guide post 42 of a corresponding pair of adjacent guide posts 42. For example, as shown, each of the four radially arranged guide posts 42 can comprise an inner recess surface 41 that faces the central axis of the central opening of the back plate 14.

In some embodiments, as shown, the guide posts 42 can be identical to one another but are geometrically twisted ±45° about the guide post axis relative to adjacent guide posts such that the inner recess surface 41 of each of the four radially arranged guide posts 42 faces the central axis of the central opening of the back plate 14. In some embodiments, the inner recess surfaces 41 of the guide posts 42 can provide clearance for an optional locking ring 16 that may be placed on a second recessed seat 44 of the implantation end 36.

As further shown in FIG. 5, the guide ridges 38, 40 may extend approximately 75% of the overall height of the back plate 14 seated on the first seat 37 of the implantation end 36 and a width sized not to exceed the outer diameter of the back plate 14. As further shown, the guide ridges 38, 40 may further have tapered leading ends 39 to aid in insertion of the implantation end into the eye during the surgical implantation procedure. As shown in FIG. 3, the implantation end 36 may further include the second recessed seat 44, which is configured to receive the optional locking ring 16 of the back portion of the artificial cornea 10 (see FIG. 4).

Turning back to FIG. 2, the thumbscrew 34 of the surgical device 30 can include a stem 50 with external threads 52, and a cap 54. During the implantation process, as further detailed below, the external threads 52 of the stem 50 can mate with the internal threads 48 of the drive nut 46 such that rotation of the thumbscrew 34 relative to the drive nut 46 adjusts an axial position of the thumbscrew 34 relative to the drive nut 46. The cap 54 provides a gripping portion by which the surgeon can turn the thumbscrew 34 relative to the drive nut 46. A distal end 56 of the stem 50 opposite from the cap 54 is configured to press against an outer surface of the front plate 12 during implantation of the artificial cornea 10. Accordingly, the thumbscrew 34 should be made of a rigid plastic material that would not scratch the front plate 12. To further prevent scratching, the distal end 56 may be specially finished with a scratch-preventing finishing material 57 (see FIG. 9) such as for example a #6 diamond buff Balance 320 paper finish. In further embodiments, the tip of the distal end 56 may comprise soft material of the type that is not hard enough to scratch the front plate 12.

Figure 4:
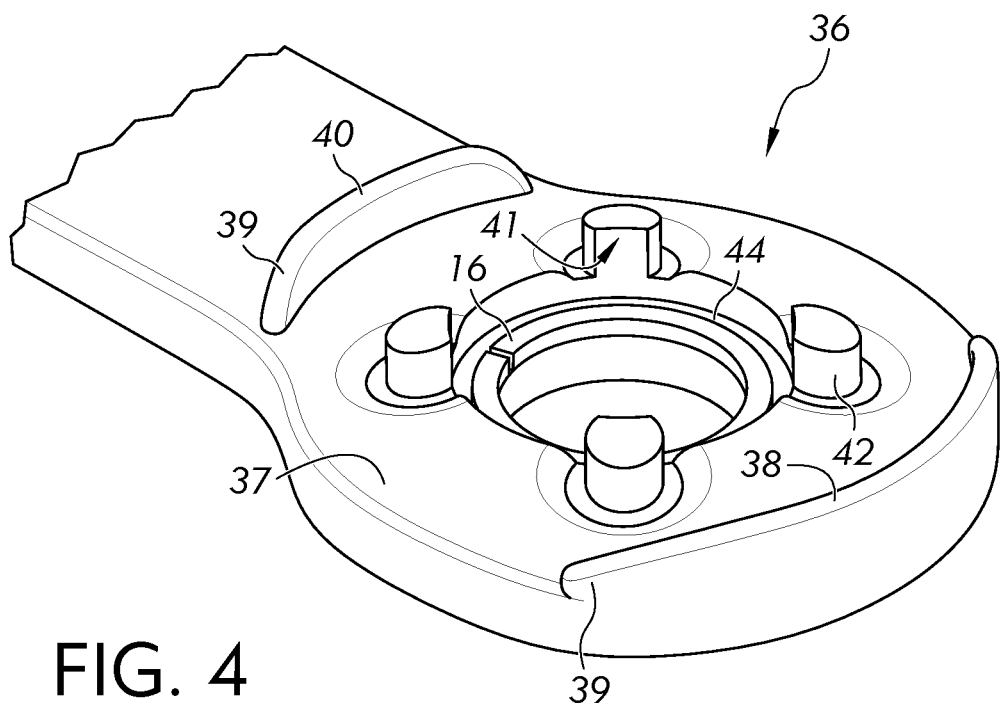
FIG. 4 illustrates an optional step in a method of performing a surgical implantation of the artificial cornea with the surgical device of FIG. 2 comprising placing an optional locking ring of a back portion of an artificial cornea on a recessed seat of the implantation end of FIG. 3.

FIGS. 4-12 illustrate the steps of methods of performing a surgical implantation of the artificial cornea 10 with the surgical device 30. An example order of the steps will be described with the understanding that, unless otherwise noted, the steps may be performed in a different order. The method can comprise the step of placing the back portion (e.g., back plate 14, optional locking ring 16) onto the implantation end 36 of the installation tool 32 externally from the eye 60 of the patient. For example, if the back portion is provided with the locking ring 16, as shown in FIG. 4, the locking ring 16 of the back portion can be placed on the recessed seat 44 of the implantation end 36 prior to placing the back plate 14. As shown in FIG. 5, the placing the back portion of the artificial cornea 10 can also comprise placing the back plate 14 of the back portion onto the first seat 37 of the implantation end 36 and using the guide posts 42 and the guide ridges 38, 40 of the first seat 37 to guide the back plate 14 onto the first seat 37. In some embodiments, the method may not include placing the locking ring 16, for example, when the stem 23 of the front plate 12 is designed to connect directly to the back plate 14 without the locking ring 16. Alternatively, as discussed below, the locking ring 16 can be provided to connect the stem 23 of the front plate 12 to the back plate 14.

Figure 6:
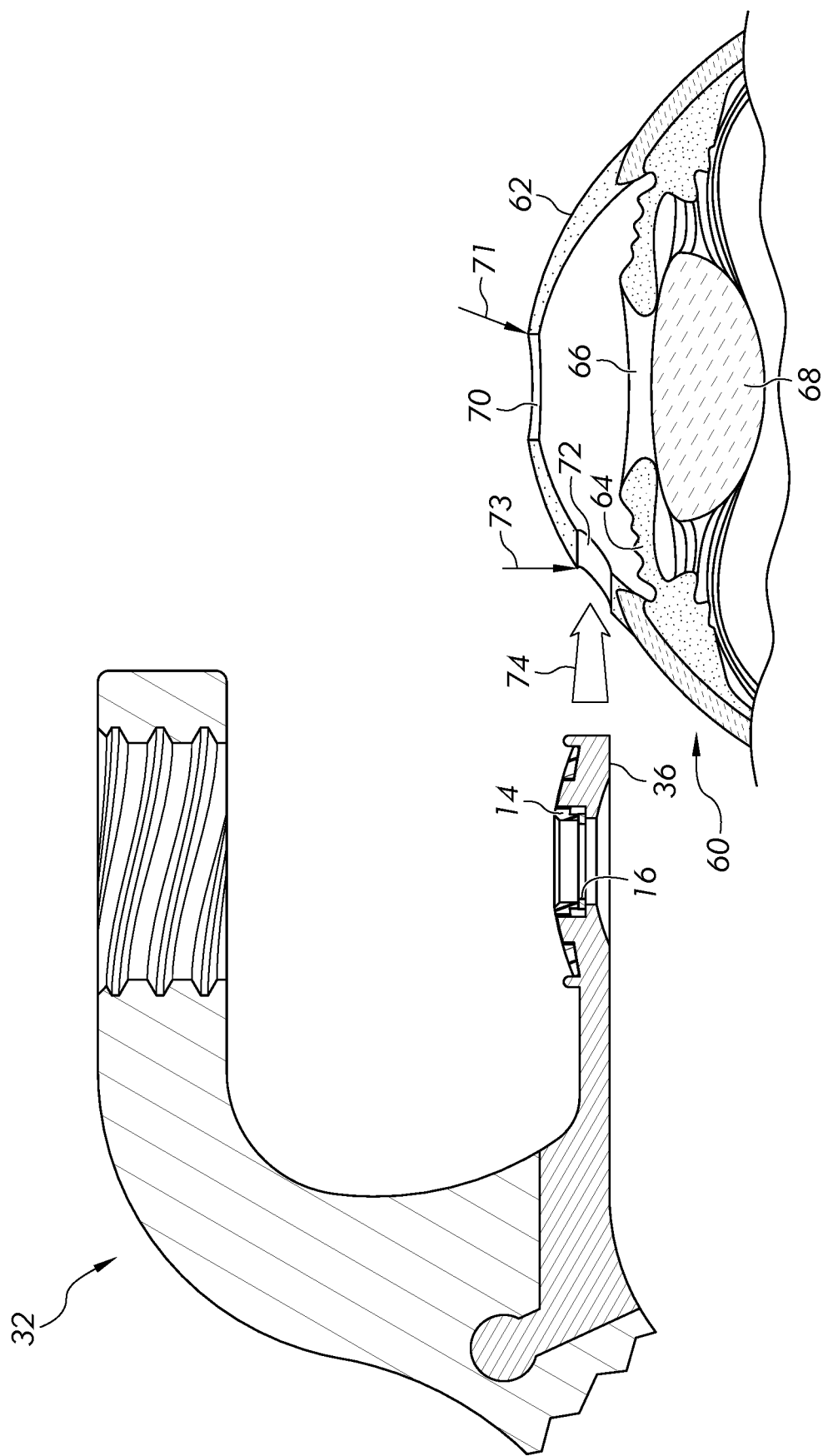
FIG. 6 schematically illustrates further steps in a method of performing a surgical implantation of the artificial cornea comprising cutting a vision hole into a cornea of a patient's eye, cutting an incision into the eye, and moving the surgical device to insert the implantation end with the back portion of the artificial cornea of FIG. 5 through the incision and into the eye.

FIG. 6 schematically illustrates an anatomy of an eye 60 of the patient including the cornea 62, iris 64, pupil 66 and lens 68. The method of performing the surgical implantation of the artificial cornea 10 with the surgical device 30 can include cutting an incision 72 into the eye 60 as schematically illustrated by arrow 73 and cutting a vision hole 70 into the cornea 62 of a patient's eye 60 as schematically illustrated by arrow 71. Cutting the vision hole 70 removes a portion of the damaged cornea to permit the passage of light for vision.

Figure 7:
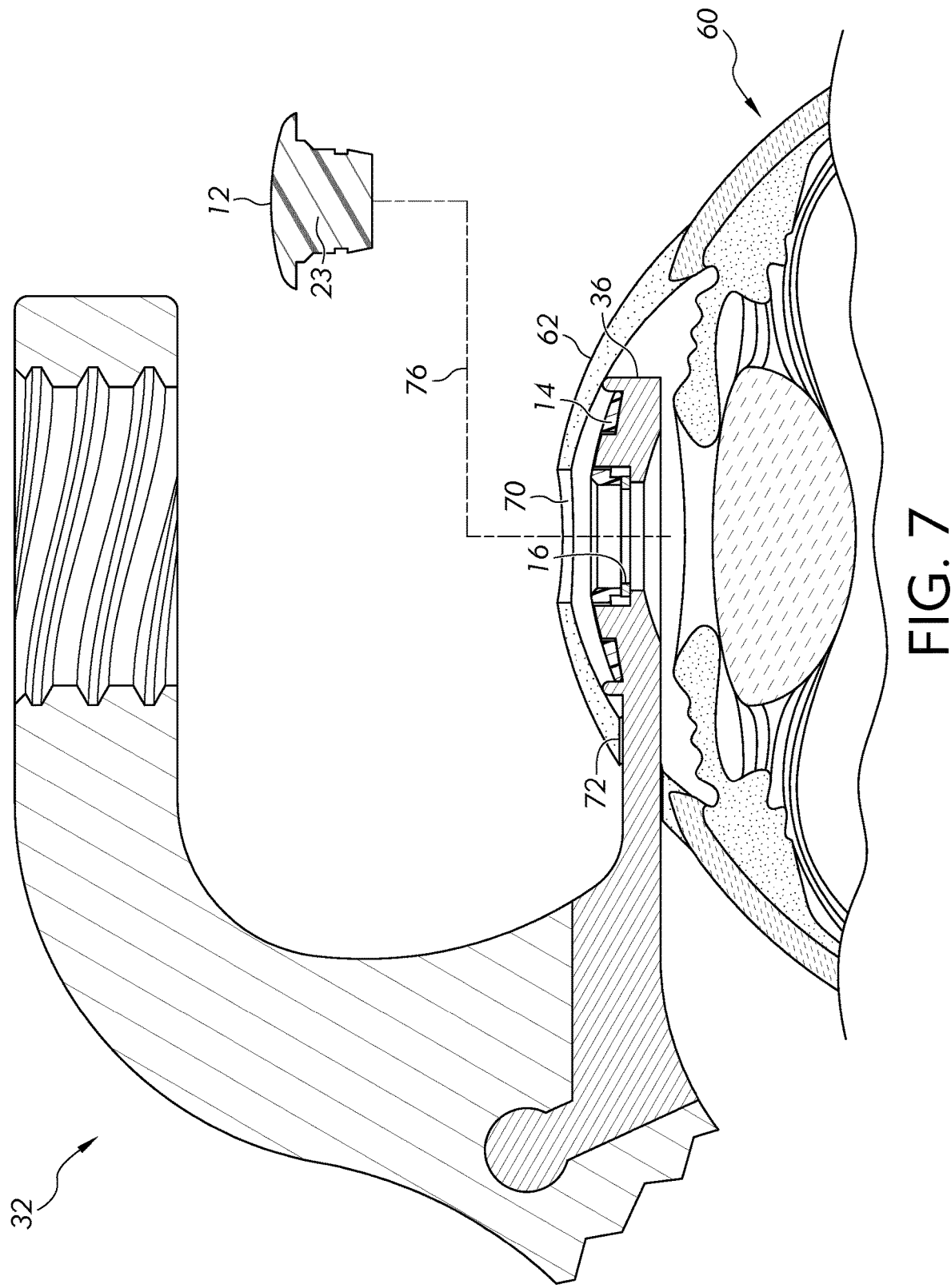
FIG. 7 schematically illustrates aligning the back portion of the artificial cornea with the vision hole and placing a front portion of the artificial cornea over the vision hole in alignment with the back portion.
Figure 8:
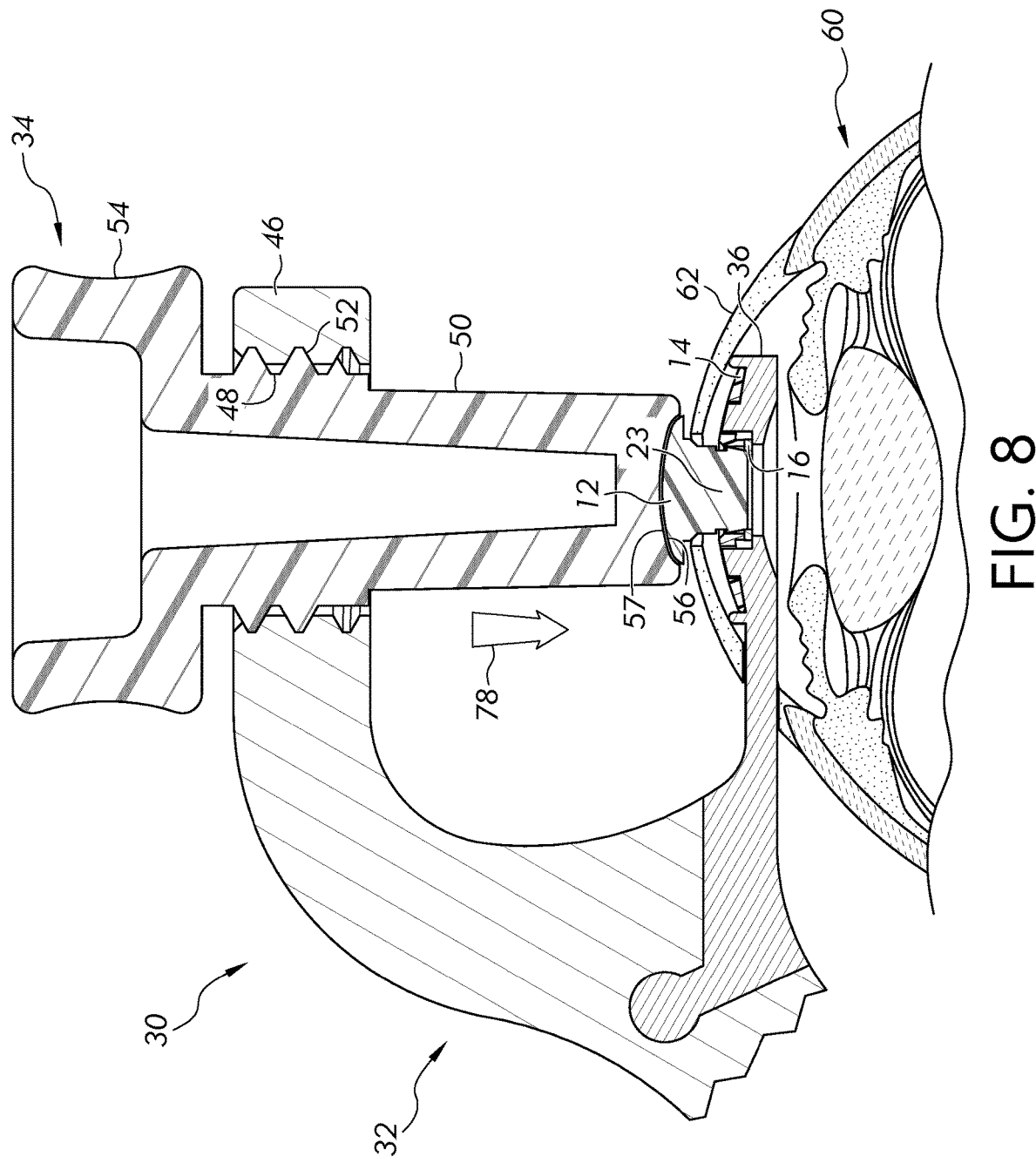
FIG. 8 schematically illustrates the front portion of the artificial cornea placed over the vision hole in alignment with the back portion.
Figure 10:
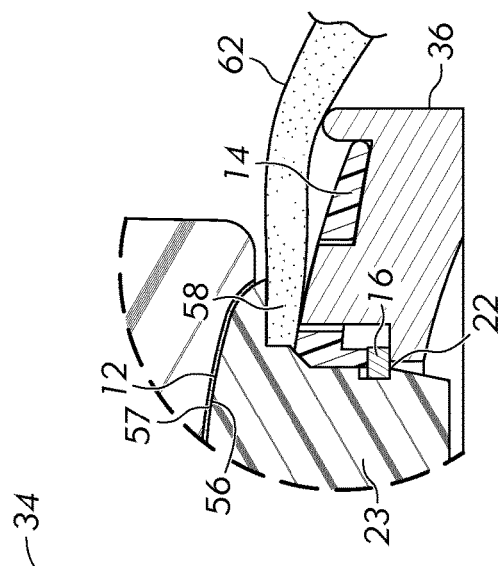
FIG. 10 is an enlarged view of the optional locking ring locked onto the front plate taken at view 10 of FIG. 9.
Figure 9:
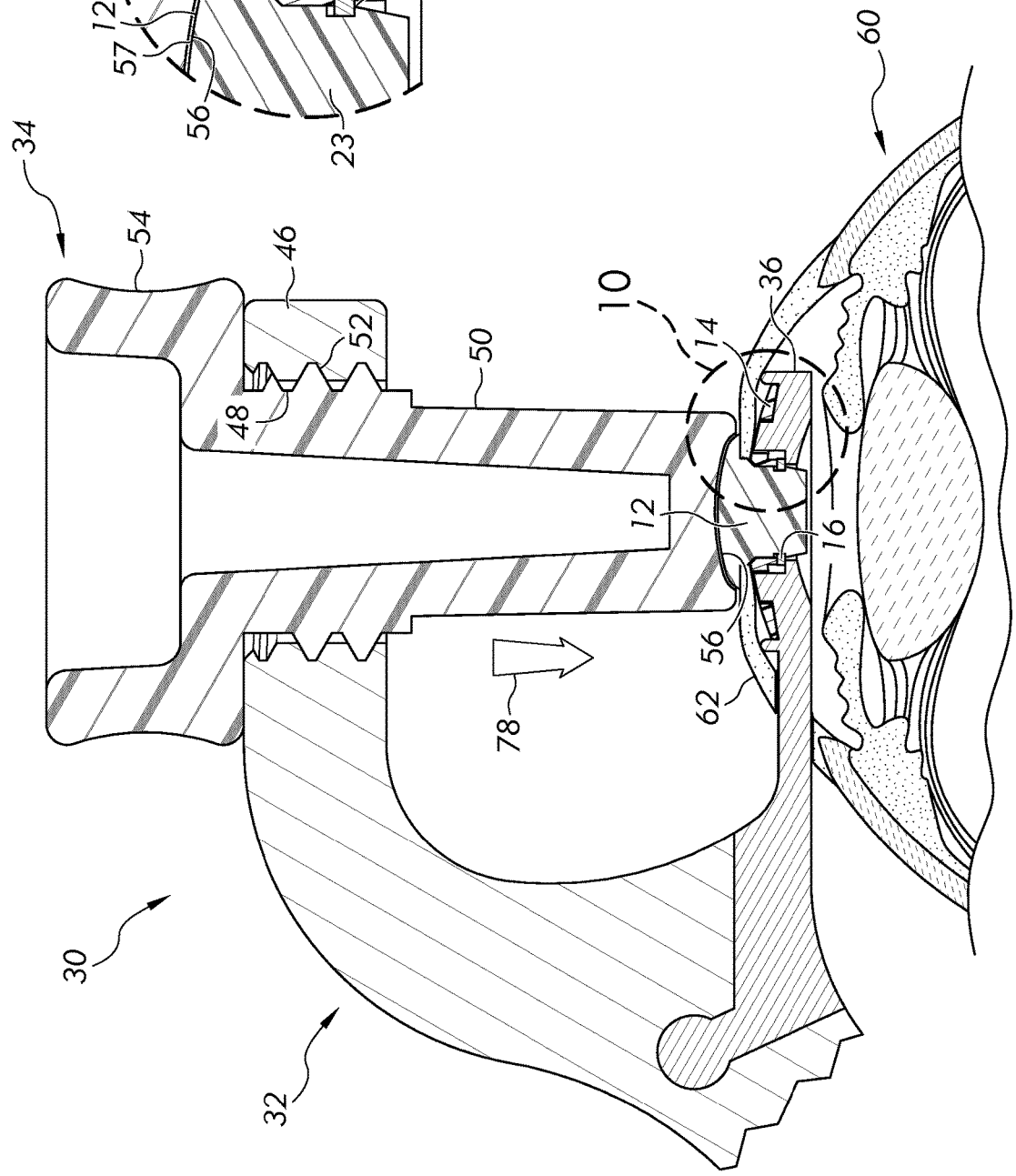
FIG. 9 schematically illustrates rotating the thumbscrew relative to the drive nut to press the front portion toward the back portion to lock the artificial cornea to the cornea of the patient's eye.

The installation tool 32 can then be moved in direction 74 to insert the implantation end 36 with the back portion of the artificial cornea 10 through the incision 72 and into the eye 60 as shown in FIG. 7. During insertion of the implantation end 36 through the incision 72, the guide ridges 38, 40 can help guard the back plate 14 from being unseated from the implantation end 36 by the patient's cornea 62 at the incision 72. As further shown in FIG. 7, the method can comprise aligning the back portion (e.g., back plate 14, locking ring 16) of the artificial cornea 10 with the vision hole 70 and then placing the front portion (e.g., front plate 12) of the artificial cornea 10 over the vision hole 70 in alignment with the back portion (e.g., back plate 14, locking ring 16) as shown by broken arrow 76. As shown in FIG. 8, once the front plate 12 is placed over the vision hole 70, the front plate 12 is in alignment with the back plate 14 with the stem 23 passing through the vision hole 70 and the central opening of the back plate 14. As shown in FIG. 8, the external threads 52 of the thumbscrew 34 can be threaded on the internal threads 48 of the drive nut 46. The thumbscrew 34 can then be rotated to drive the thumbscrew in axial direction 78 relative to the drive nut 46 until the distal end 56 of the stem 50 of the thumbscrew 34 engages the outer surface of the front plate 12 as shown in FIG. 8. Although not shown, the thumbscrew can be initially partially threaded onto the drive nut while the implantation end 36 is exterior of the eye 60 (e.g., in the position shown in FIG. 6). As shown in FIG. 9, the method comprises further rotating thumbscrew 34 relative to the drive nut to press the front portion toward the back portion to lock the artificial cornea 10 to the cornea 62 of the patient's eye 60. In some embodiments, the thumbscrew 34 can be rotated until the locking ring 16 locks onto the front plate 12. For example, as shown in FIG. 10, after the stem 23 is fully inserted by rotating the thumbscrew 34, the locking ring 16 can snap behind the ridge 22 on the stem 23 to lock the artificial cornea 10 in place relative to the cornea 62 of the patient. Once the locking ring 16 is snapped behind the ridge 22, as further shown in FIG. 10, an inner peripheral portion of the cornea 62 defining the vision hole 70 is trapped and pinched in the gap 58 located between the front plate 12 and the back plate 14, thereby locking the artificial cornea 10 to the cornea 62 of the eye 60 of the patient.

Once the artificial cornea 10 is locked in place relative to the cornea 62, as shown in FIG. 11, the method can include the step of moving the implantation end 36 of the installation tool 32 out of the incision 72 to remove the implantation end 36 of the installation tool 32 from the patient's eye 60 while leaving the artificial cornea 10 locked to the cornea 62 of the patient's eye 60. During the step of removing the implantation end 36, the implantation end 36 can be first moved in direction 80 to disengage the guide posts 42 from the back plate 14 before moving the implantation end 36 in direction 82 to remove the implantation end 36 from the patient's eye 60.

With the surgical device and method of the present disclosure, therefore, the artificial cornea 10 can be implanted without assembling the artificial cornea to an extracted cornea section that needs to then be sutured into place to close a large opening previously cut into the eye. Rather, features of the disclosure involve cutting a single, significantly smaller incision into the eye for inserting the implantation end 36 of the surgical device 30 into the eye with the back portion of the artificial cornea placed thereon. The actual implantation process is performed directly on the eye with minimal suturing and without the additional surgical steps used in conventional methods. The surgical procedure associated with the present disclosure, therefore, is more efficient, far less invasive, and obviates the need for removal and suturing back of the cornea section, and therefore should result in a reduced complication rate.

Although the disclosure has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the disclosure. In addition, while a particular feature of the disclosure may have been described above with respect to only one or more of several illustrated embodiments, such feature may be combined with one or more other features of the other embodiments, as may be desired and advantageous for any given or particular application.

What is claimed is:

1. A surgical device for implanting an artificial cornea into an eye, the surgical device comprising:
    an installation tool comprising an implantation end for receiving a back portion of an artificial cornea, and a drive nut positioned above the implantation end, the implantation end comprising a first seat for receiving a back plate of the back portion of the artificial cornea, and a plurality of guide posts that extend from the first seat to guide locating of the back plate, wherein each guide post of the plurality of guide posts are positioned between a pair of adjacent guide posts of the plurality of guide posts, wherein each guide post of the plurality of guide posts are twisted 45° relative to each guide post of a corresponding pair of adjacent guide posts; and
    a thumbscrew that is received within the drive nut, the thumbscrew being rotatable relative to the drive nut to adjust a position of the thumbscrew,
    wherein during an implantation procedure, the implantation end with the back portion of the artificial cornea positioned thereon is inserted into the eye, and the thumbscrew is rotated relative to the drive nut to interact against a front portion of the artificial cornea to lock the artificial cornea in place.

2. The surgical device of claim 1, wherein the implantation end further comprises a plurality of guide ridges to further guide locating of the back plate.

3. The surgical device of claim 2, wherein the guide ridges comprise tapered ends to aid in inserting the implantation end into the eye.

4. The surgical device of claim 1, wherein the implantation end further comprises a recessed seat for receiving a locking ring of the back portion of the artificial cornea.

5. The surgical device of claim 1, wherein the drive nut and the thumbscrew comprise opposing cooperating threads to permit rotating the thumbscrew relative to the drive nut.

6. The surgical device of claim 5, wherein the thumbscrew comprises:
   a stem comprising threads opposing threads of the drive nut;
   a cap located on the stem that comprises a gripping portion for rotating the thumbscrew relative to the drive nut; and
   a distal end located opposite from the cap that interacts against a front plate of the front portion of the artificial cornea.

7. The surgical device of claim 6, wherein the distal end has a finished surface to prevent scratching the front plate.

8. The surgical device of claim 1, wherein the installation tool comprises titanium or surgical grade stainless steel.

9. The surgical device of claim 1, wherein the thumbscrew comprises plastic.

10. The surgical device of claim 1, wherein the installation tool comprises a handle portion that ends in the drive nut, and the handle portion and the implantation end comprise a unitary piece.

11. The surgical device of claim 1, wherein the installation tool comprises a handle portion that ends in the drive nut, and the handle portion and the implantation end are separate components fixed together at a joint.

12. The surgical device of claim 1, wherein the drive nut and the implantation end are spaced apart by a distance between 5.2 mm and 12.2 mm.

13. A surgical device for implanting an artificial cornea into an eye, the surgical device comprising:
   an installation tool comprising an implantation end for receiving a back portion of an artificial cornea, and a drive nut positioned above the implantation end, wherein the drive nut and the implantation end are spaced apart by a distance between 5.2 mm and 12.2 mm; and
   a thumbscrew that is received within the drive nut, the thumbscrew being rotatable relative to the drive nut to adjust a position of the thumbscrew,
   wherein during an implantation procedure, the implantation end with the back portion of the artificial cornea positioned thereon is inserted into the eye, and the thumbscrew is rotated relative to the drive nut to interact against a front portion of the artificial cornea to lock the artificial cornea in place.

14. The surgical device of claim 13, wherein the implantation end comprises a first seat for receiving a back plate of the back portion of the artificial cornea, and a plurality of guide posts that extend from the first seat to guide locating of the back plate.

15. The surgical device of claim 13, wherein the drive nut and the thumbscrew comprise opposing cooperating threads to permit rotating the thumbscrew relative to the drive nut.

16. The surgical device of claim 15, wherein the thumbscrew comprises:
   a stem comprising threads opposing threads of the drive nut;
   a cap located on the stem that comprises a gripping portion for rotating the thumbscrew relative to the drive nut; and
   a distal end located opposite from the cap that interacts against a front plate of the front portion of the artificial cornea.

17. A method of performing a surgical implantation of an artificial cornea with a surgical device comprising: an installation tool comprising an implantation end, and a drive nut positioned above the implantation end, and a thumbscrew that is received within the drive nut, the method comprising the steps of:
   placing a back portion of an artificial cornea onto the implantation end of the installation tool externally from an eye of a patient by placing a back plate of the back portion onto a first seat of the implantation end and using guide posts of the first seat to guide the back plate onto the first seat;
   cutting a vision hole into a cornea of the eye;
   cutting an incision into the eye;
   inserting the implantation end with the back portion of the artificial cornea through the incision and into the eye;
   aligning the back portion of the artificial cornea with the vision hole;
   placing a front portion of the artificial cornea over the vision hole in alignment with the back portion;
   rotating the thumbscrew relative to the drive nut to press the front portion toward the back portion to lock the artificial cornea to the cornea of the eye; and
   moving the implantation end out of the incision to remove the implantation end of the installation tool from the eye while leaving the artificial cornea locked to the cornea of the eye.

18. The surgical implantation method according to claim 17, wherein, after placing the back plate, distal ends of the guide posts are flush with an outer surface of the back plate.

19. The surgical implantation method according to claim 17, further comprising, prior to placing the back plate, placing a locking ring of the back portion of the artificial cornea on a recessed seat of the implantation end.

20. The surgical implantation method of claim 19, wherein the rotating the thumbscrew rotates the thumbscrew until the locking ring locks onto the front plate.

* * * * *